United States Patent [19]

Decker et al.

[11] Patent Number: 5,469,731
[45] Date of Patent: Nov. 28, 1995

[54] APPARATUS AND METHOD FOR A GAS QUANTITY SETTING SYSTEM

[75] Inventors: Hans-Josef Decker, Ronnenberg; Klaus-Peter Schwarz, Burgdorf, both of Germany

[73] Assignee: Siemens Aktiengesellschaft, München, Germany

[21] Appl. No.: 145,938

[22] Filed: Nov. 2, 1993

[30] Foreign Application Priority Data

Nov. 2, 1992 [DE] Germany .......................... 42 37 009.4
Jul. 15, 1993 [EP] European Pat. Off. ............... 93111433

[51] Int. Cl.$^6$ ............................ G01M 15/00; G01N 1/22
[52] U.S. Cl. .................... 73/23.31; 73/23.41; 73/863.03; 73/864.81
[58] Field of Search ............... 73/23.21, 23.31, 73/23.32, 23.33, 23.41, 863.03, 863.22, 864.81

[56] References Cited

U.S. PATENT DOCUMENTS

| 1,658,391 | 2/1928 | Potter | 73/23.31 |
|---|---|---|---|
| 1,904,819 | 4/1933 | Blodgett | 73/23.31 |
| 3,603,155 | 9/1971 | Morris | 73/863 |
| 3,668,834 | 6/1972 | Deans | 73/864.81 |
| 3,699,814 | 10/1972 | Kaufman | 73/23.31 |
| 3,965,749 | 6/1976 | Hadden et al. | 73/421.5 |
| 4,586,367 | 5/1986 | Lewis | 73/23 |
| 4,751,907 | 6/1988 | Yamamoto et al. | 73/23.32 |
| 4,869,094 | 9/1989 | Kozuka et al. | 73/864.81 |
| 5,113,689 | 5/1992 | Piade et al. | 73/23.21 |
| 5,178,022 | 1/1993 | Tomlin | 73/864.81 |
| 5,218,857 | 6/1993 | Decker et al. | 73/23.31 |
| 5,337,595 | 8/1994 | Lewis | 73/23.31 |

FOREIGN PATENT DOCUMENTS 9014528.3  2/1991  Germany .
1280474A   12/1986  U.S.S.R. .

Primary Examiner—Richard Chilcot
Assistant Examiner—George M. Dombroske
Attorney, Agent, or Firm—Kenyon & Kenyon

[57] ABSTRACT

A gas quantity setting system, such as for the testing and/or certification of "low emission vehicles", provides a dilution air/exhaust gas mixture for investigation and has a continuously cross-sectionally variable, venturi nozzle and an axially adjustable conical, nozzle needle. The nozzle needle of the venturi nozzle is adjustable by a computing device, taking into consideration a temperature, a pressure and measured values of a mass rate of flow meter, in such a way that a dilution ratio (dilution factor) of the exhaust gas has a predetermined, preferably constant, value in spite of fluctuations in the feeding of quantities of exhaust gas.

18 Claims, 4 Drawing Sheets

APPARATUS AND METHOD FOR A GAS QUANTITY SETTING SYSTEM

BACKGROUND OF THE INVENTION

1. Field of the Invention

The present invention relates to a device and an operating process for a gas quantity setting system, such as for the testing and/or certification of "low emission vehicles". In such systems a dilution air/exhaust gas mixture is taken for investigation. According to the present invention the system has a cross-sectionally variable, in particular continuously cross-sectionally variable, venturi nozzle with an axially adjustable, preferably conical, nozzle needle. The nozzle needle of the venturi nozzle is adjustable using a computing device, taking into consideration a temperature, a pressure and measured values of a mass rate of flow meter, in such a way that the dilution ratio (dilution factor) of the exhaust gas has a predetermined, preferably constant, value despite fluctuations in the feeding of quantities of exhaust gas.

2. Related Art

Gas quantity setting systems for the testing of vehicle exhaust gases are known, for example from U.S. Pat. No. 4,586,367 and from U.S. Pat. No. 3,603,155. These known systems operate with an average dilution rate, in order to determine the concentration of pollutants. The average dilution rate inevitably provides only an integral value overtime and it is not possible to ascertain an instantaneous result (for example in acceleration phases). Therefore, incorrect statements concerning the actual conditions are not ruled out. In fact, the conditions are changing constantly between exhaust gas and dilution air, since a driving cycle of the vehicle requires accelerations, decelerations etc., which leads to different exhaust gas/dilution air ratios.

German Utility Model G 90 14 528 discloses an exhaust gas quantity setting device which is more suitable when compared to the systems in the two U.S. patents referred to above. The integral evaluation is replaced by a direct evaluation. Thus, it becomes possible for the interrelationship of exhaust gas concentration and exhaust gas quantity with unique assignment to be modal, i.e., in predetermined sample quantities. The above-mentioned devices operate with known critical venturi nozzles, which set the desired total rate of flow quantities.

SUMMARY OF THE INVENTION

The present invention provides a device and an operating process for a gas quantity setting system which is more suitable, preferably for testing and/or certification purposes of "low emission vehicles" without concern for variations of exhaust gas due to changes in the driving cycle. In the case of "low emission vehicles", the expected quantities of pollutants in the exhaust gas in the future, or in some cases already achieved today, are very low. Therefore, in the case of a downstream exhaust gas analysis installations or particle measuring devices having a large quantity of gas as in the known systems, the detection limit is reached. The measuring errors occurring are correspondingly great. According to the present invention, therefore, the aim is to make available to the analysis devices or particle measuring devices a gas mixture which ensures a reliable, accurate detection of the concentrations of pollutants. At the same time, the aim is for it also to be possible to draw conclusions concerning changes in the concentrations of pollutants by means of simple time-quantity comparisons.

The present invention provides a means adapted to the respective quantity of exhaust gas for controlling a cross-sectionally variable, in particular continuously cross-sectionally variable, venturi nozzle for setting a dilution factor which is optimal at all times.

It is provided in this case that the respective, driving-state-dependent exhaust gas volume of the vehicle to be tested, that is in particular of the "low emission vehicle", is continuously converted into positional changes of the nozzle needle to maintain a dilution ratio which is optimal for an exhaust gas analysis or particle measurement. The composition of the dilution air/exhaust gas mixture, which is taken from the gas quantity setting system, is thus kept in a range that optimizes the gas analysis and/or particle quantity measurement.

In an embodiment of the present invention it is provided that the total flow quantity is set by means of a controller relying on actual and desired values. The intention here is to improve the behavior of the control which, in particular when there are abrupt gas quantity changes in the system, performs an advance setting of the nozzle needle position to be expected, taking into consideration the system inertia. This is carried out in particular by a fuzzy-control unit, which is supplied with corresponding if-then rules, for example in dependence on the setting of the carburetor or of the injection system. The dilution air is advantageously kept in a predetermined temperature range during operation, in order to avoid drops below the dew point or excessive heating up of the system.

The invention is advantageously carried out with a gas quantity setting system which has an adjustable, preferably controllable, conical, nozzle, for example a venturi nozzle with position-controlled nozzle needle. The position control of the nozzle needle advantageously has a characteristic correcting device to increase the accuracy of the setting. This may be supplemented by a fuzzy-control unit for intervention in the event of abrupt changes in the driving state of the tested vehicle.

In the advantageous configuration shown by way of example, the position-controlled nozzle needle has an axial adjustment spindle with drive motor and fixed bearing on the motor side and also a ball-threaded bush, preferably with great pitch, in engagement with the axial adjustment spindle. It is advantageously mounted axially displaceably in a guide cylinder or cage and has a conical diffuser adaptation tip with a cylindrical run-in section, rounded at the front. This produces a particularly good characteristic profile.

For connection with a higher-level control system, for example a test bench, an interface unit is provided, as well as a computing unit. Preferably the computing unit has a "touch screen" for entering the desired dilution factor and operating commands. A subunit may be provided for carrying out correction calculations on the basis of characteristics and for processing fuzzy-control improvements of the control, if they prove to be necessary.

The present invention is explained in more detail with reference to drawings, from which, further details of the invention are evident.

DETAILED DESCRIPTION

Figure 1:
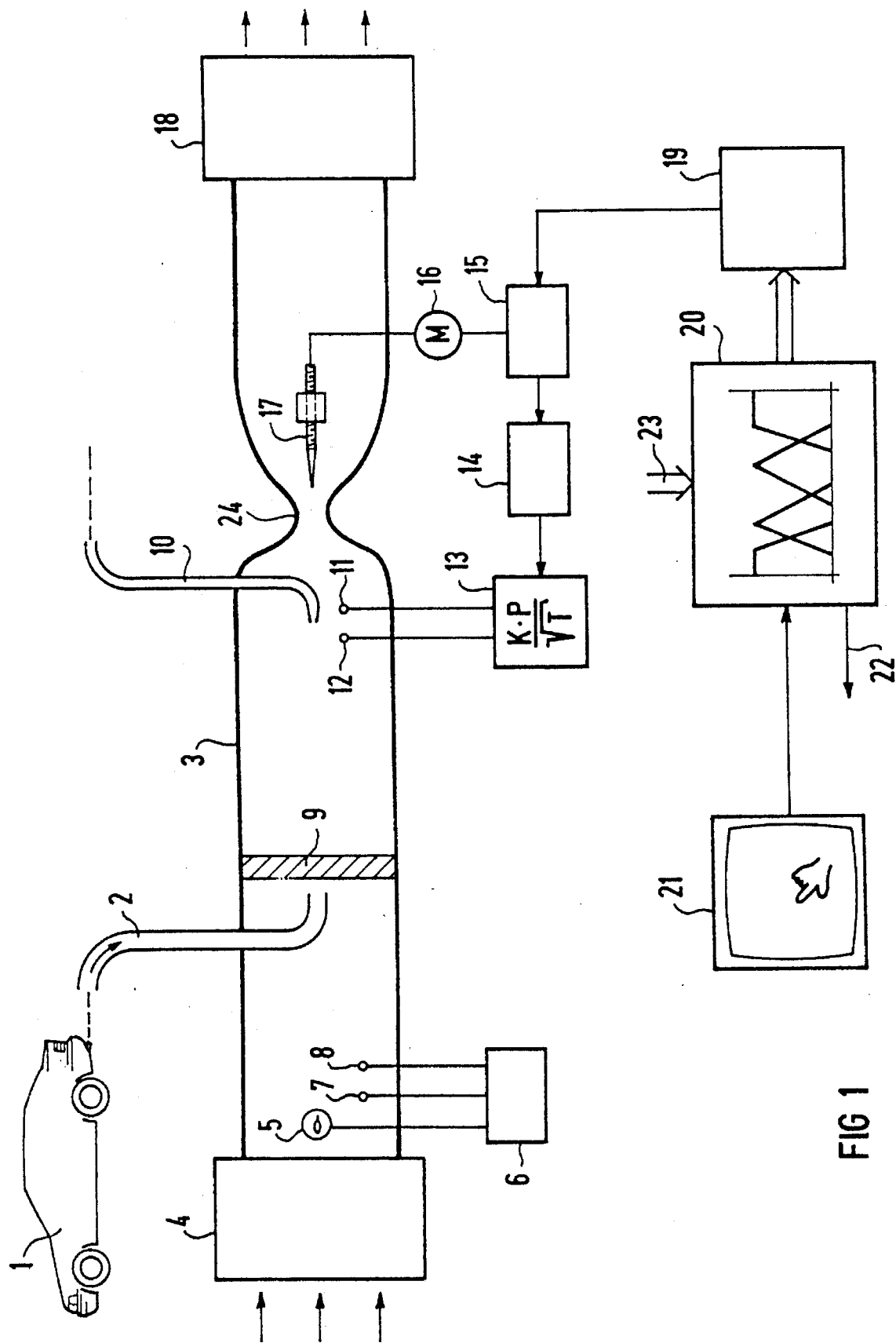
FIG. 1 shows a control structure of a gas quantity setting system according an embodiment of the invention.

In FIG. 1, a motor vehicle, 1, produces an exhaust gas which is fed through a supply line 2 to a system according to an embodiment of the present invention. The gas quantity setting system itself has, in an advantageously simple way, a tubular main flow element 3, which is connected to a dilution air filter 4. In the flow path there is located, downstream of the dilution air filter 4, a vortex probe 5, known per se, with temperature and pressure measuring points 8 and 7. A computing unit 6 calculates the quantity of dilution air from the values of the vortex probe 5 and the pressure P and also the temperature T. In the flow path there is located, downstream of the supply line for the exhaust gas 2, in the tubular element 3, a mixer 9, for example a perforated disk, a coarse-meshed screen or the like. Similarly, however, a swirl mixer may also be used.

A sampling tube 10 is disposed in an advantageously flow-stabilized region of the tubular element 3. Pressure and temperature measuring sensors 12 and 11 are also arranged in that region. These sensors supply their measured values to a computing unit 13, the basic algorithm of which is specified. The sampling tube receives part of the gas stream for measurement. A venturi nozzle 22 with an adjustable nozzle needle 17, is located downstream of the sampling tube 10. A turbo-compressor, for example a Roots blower 18, adjoins the venturi nozzle. However, a water-ring gas pump or similar positive-displacement pump may also be arranged here.

The nozzle needle 17 is motor-adjustable, for example by a motor 16, the position of which is under the control of positioning control 15. By means of a computing unit, in which the characteristic for the relationship between volume flow and position is stored, the actual dilution factor is then calculated in 13 with the information from the pressure and temperature probes 11 and 12. The unit 19, in which a manipulated-variable correction of the needle position is performed, acts on the positioning control 15. This control is either directly the result of a signal from the "touch screen" 21 (entry of the dilution factor) or of a unit 20 in which a superposed fuzzy control takes place.

The dilution factor 23 from the computing units 6 and 13 is supplied either directly to the computing unit of the "touch screen" 21 or, as shown, to the unit 20. The actual value of the dilution factor is then passed on by the output arrow 24 to a control system or else to the "touch screen" 21. Thus, either a direct, or else a higher-level, observation and consideration of the actual value of the dilution factor and its deviations from the desired value is possible.

Figure 2:
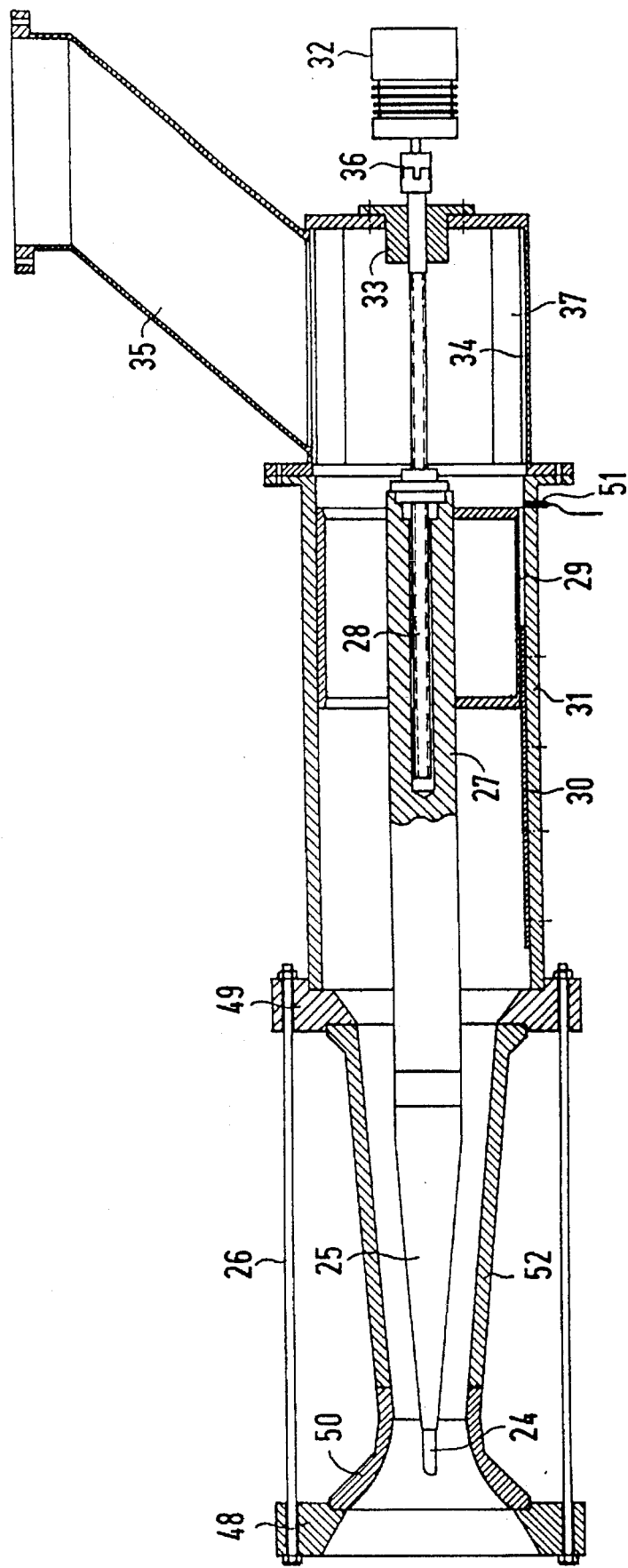
FIG. 2 shows a detailed section through a crosssectionally variable venturi nozzle of the embodiment of FIG. 1.

In FIG. 2, which shows the mechanical construction of the cross-sectionally variable venturi nozzle (shown as 24 in FIG. 1), 52 denotes the diffuser part of the venturi nozzle and 50 denotes its run-in part. The two parts 52 and 50 are held by clamping flanges 48 and 49. The clamping flanges 48 and 49 are fixed by anchors 26. The nozzle needle 25, with the cylindrical run-in section 24 rounded off at the front, is located inside the venturi nozzle comprising the parts 52 and 50. The conical nozzle needle section 25 adjoins a cylindrical thrust rod 27, into which the threaded rod 28 engages. As axial guidance and simultaneous securement against twisting, the thrust rod 27 has a guide cylinder or a cage 29, which is guided by screws or sliding blocks 30 (not denoted in any more detail) in the cylindrical outer shell 31 with a preferably inductive reference point switch 51. The drive of the spindle 28 for positioning the nozzle needle with the parts 24, 25 and 27 is performed by the stepping motor 32, which moves the spindle 28 by means of a coupling 36. The spindle 28, preferably a backlash-free ball spindle with great pitch, known from the field of machine tools, also has the advantageously backlash-free fixed bearing 33, which ensures that the rotation of the spindle 28 by the motor 32 leads to an axial movement of the thrust rod 27 and not to an axial movement of the axial spindle 28. The derivation of the set quantity of gas is performed by the pipe socket 35, which can branch off in the region of the spacing mounts 37 from the cylindrical part 34, which prolongs the cylindrical outer shell 31.

Figure 3:
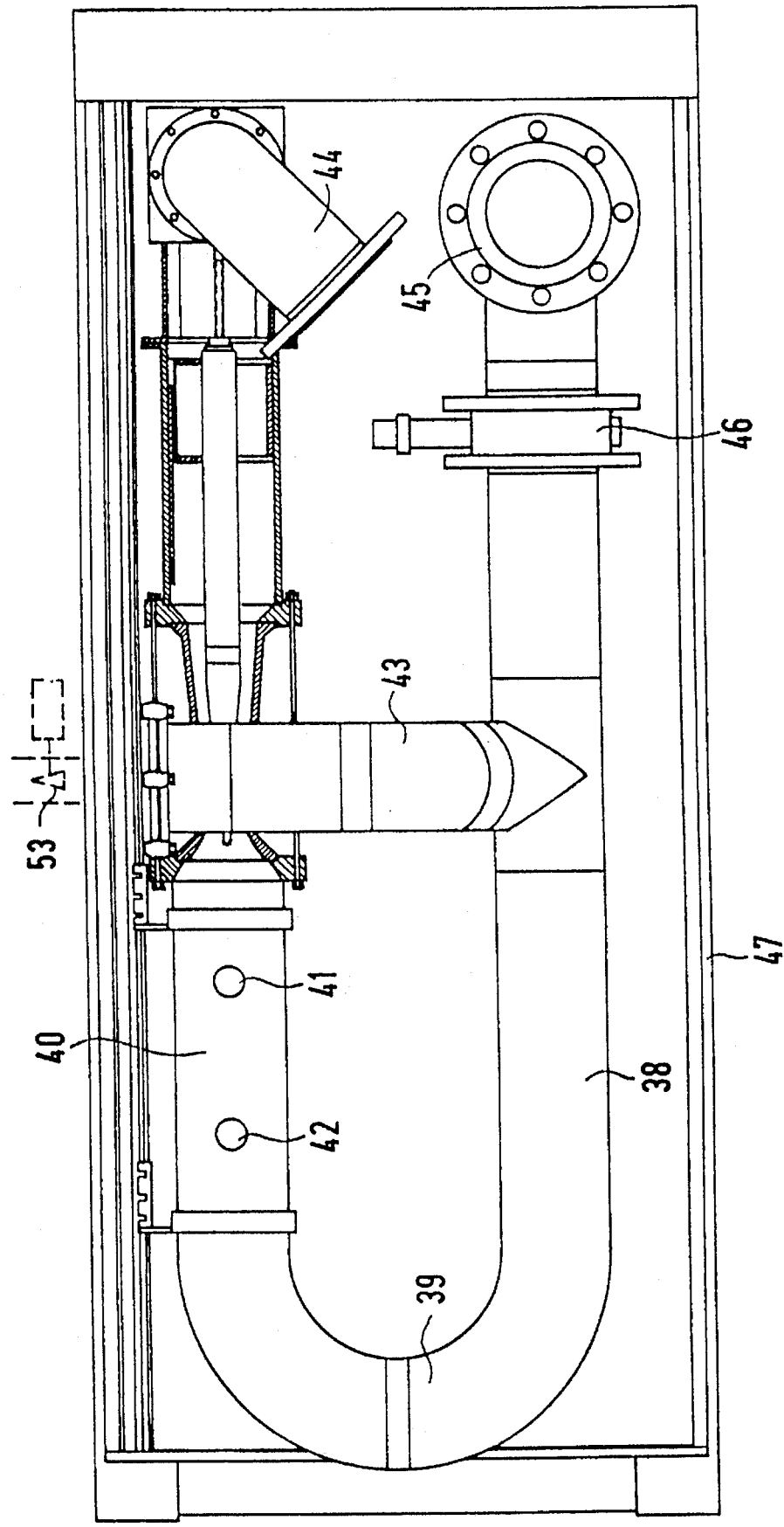
FIG. 3 shows an exemplary arrangement of the gas quantity setting system of the present invention in a test bench module.

FIG. 3 reveals a particularly space-saving arrangement of a gas quantity setting system of a motor vehicle exhaust gas analysis device in an exemplary construction, where space-saving is often required due to the structural conditions of the test benches. The feeding of ambient air is performed via the pipe socket 43 and the feeding of exhaust gas is performed via the pipe socket 45. The exhaust gas socket 45 can be blocked off by closing valve 46 that prevents gas from socket 45 from entering pipe 38, to permit a calibration of the venturi nozzle in the various positions of the nozzle needle, by a probe, for example a known vortex probe, arranged for instance upstream of the socket 43. In the run-in region 40 upstream of the venturi nozzle there are located the pressure and temperature measuring points 41 and 42, into which corresponding measuring probes are inset in a customary way. The gas quantity setting system itself is advantageously mounted in a separate frame 47, the claw mounting shown at the run-in region 40 providing a possibility of expansion for the pipes 38, 39 to compensate for the temperature effects. The configuration according to FIG. 3, provides a gas quantity setting module which can be integrated easily and simply into existing or newly planned test benches or the like.

For reasons of simplification, heating or cooling devices for controlling a temperature of gas when the system, which are also advantageously present according to the present invention, are not shown in the drawing figures since a person skilled in the art knows how to configure and arrange corresponding heating or cooling coils.

Figure 4:
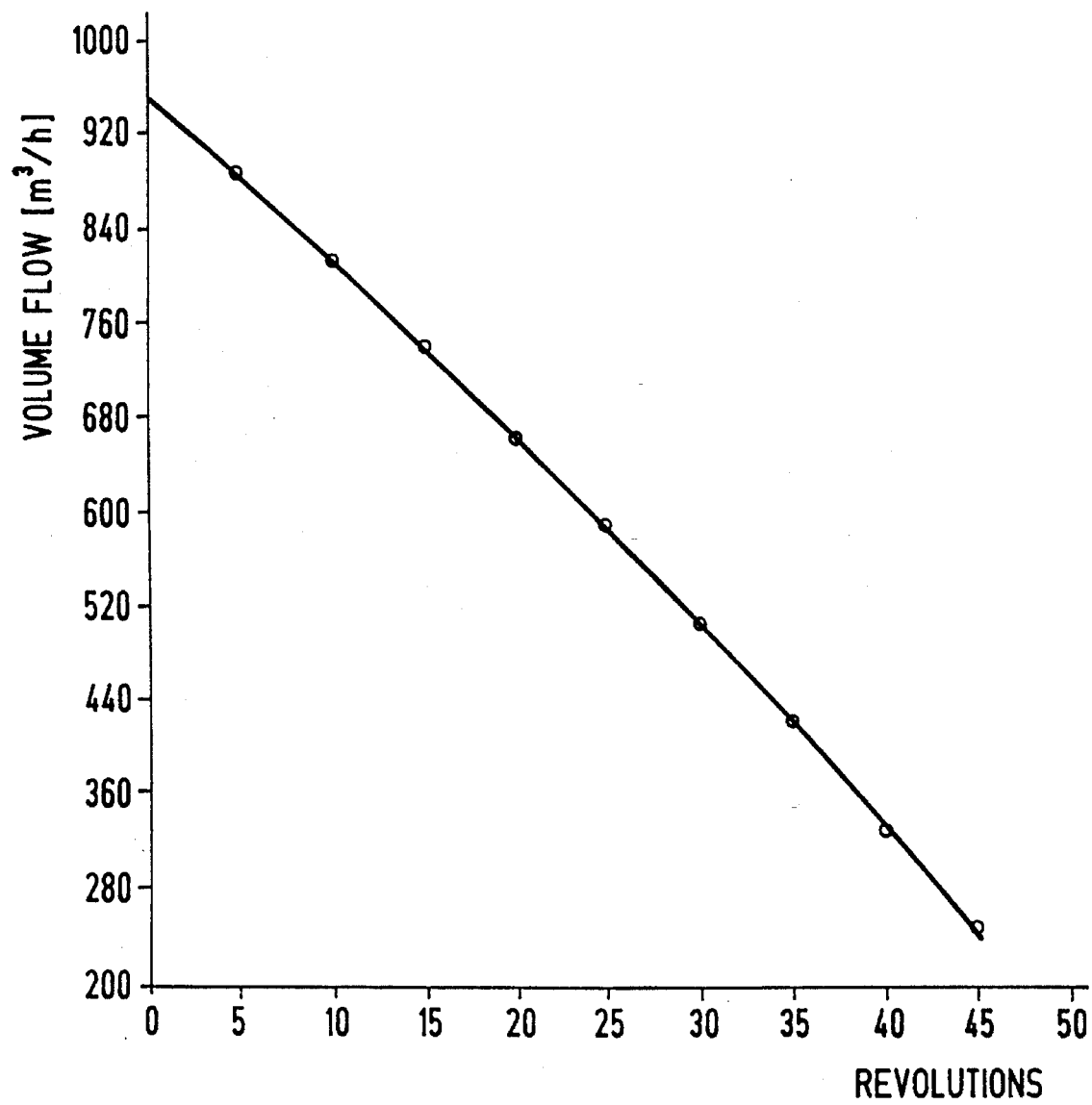
FIG. 4 shows a characteristic curve that indicates a dependence of the volume flow on the nozzle needle position.

FIG. 4 shows the dependence of the volume flow on the nozzle needle position. As can be seen, the volume flow of the critical nozzle follows virtually linearly from the number of revolutions of the setting spindle. The profile of the curve can be reproduced by a second order polynomial so that the computing device can also determine intermediate values very accurately. Such a conversion is generally customary and known from the calibration of sensors. In the use of a ball spindle customary in machine tool engineering, a repeat accuracy which lies clearly above the requirements of actual situations was achieved. For the overall gas quantity setting system, this provides the possibility of a hitherto unattainably good optimization of the dilution factor, which is important in particular for measurements on "low emission vehicles". The exhaust gas test which can be realized with the gas quantity setting system according to the present invention meets all the preconditions which are imposed, for example, on the California emissions or particle test.

What is claimed is:

1. An apparatus for a gas quantity setting system in which a mixture of dilution air and exhaust gas is sampled for analysis, the apparatus comprising:

a cross-sectionally variable, venturi nozzle, the venturi nozzle defining an axis; and an axially adjustable, conical, nozzle needle, wherein a position of the nozzle needle in the venturi nozzle is adjusted based on a temperature, a pressure and measured values of a mass rate of flow meter, such that a dilution ratio of the exhaust gas has a predetermined constant value despite fluctuations in quantities of exhaust gas fed to the apparatus.

2. The apparatus according to claim 1, wherein a volume of exhaust gas to be tested is continuously converted into positional changes of the nozzle to maintain a dilution ratio which is optimal for analysis.

3. The apparatus according to claim 1, wherein a total flow quantity of the system is automatically maintained in a range which is optimal for an analysis of a sample taken.

4. The apparatus according to claim 1, including a controller for setting the total flow quantity in accordance with a desired dilution rate and an actual dilution rate.

5. The apparatus according to claim 1, further comprising a fuzzy-control sub-unit for providing an advance setting of the nozzle needle position to be expected in accordance with a consideration of a behavior of the system in an event of abrupt gas quantity changes.

6. The apparatus of claim 1, further comprising a volume flow characteristic correcting device for controlling a position of the nozzle needle.

7. The apparatus of claim 1, further comprising a fuzzy-control unit for intervention in the control of the position of the nozzle needle in the event of abrupt changes in a rate of production of exhaust gas.

8. The apparatus of claim 1, further comprising an interface unit, for connecting the apparatus to a higher-level control system.

9. The apparatus of claim 1, wherein the position-controlled nozzle needle includes an axial adjustment spindle, a drive motor, a fixed bearing on the motor side and a ball-threaded bush engaging with the axial adjustment spindle.

10. The apparatus of claim 9, further comprising a guide cylinder wherein the nozzle needle is mounted axially displaceably in the guide cylinder.

11. The apparatus of claim 9, wherein the nozzle needle includes a conical diffuser adaptation section and a cylindrical run-in section, rounded at an end opposite of the conical diffuser adaptation section.

12. The apparatus of claim 11, further comprising:

a computing unit having a touch screen for entering a desired dilution factor and operating commands; and a sub-unit for carrying out nozzle needle position correction calculations.

13. The apparatus of claim 1, further comprising a guide cylinder wherein the nozzle needle is mounted axially displaceably within said guide cylinder.

14. The apparatus of claim 1, wherein the nozzle needle includes a conical diffuser adaptation section and a cylindrical run-in section, rounded at an end opposite of the conical diffuser adaptation section.

15. The apparatus of claim 1, further comprising:

a computing unit having a touch screen for entering a desired dilution factor and operating commands; and a sub-unit for carrying out correction calculations for positioning the nozzle needle for adaptations to measured characteristics.

16. The apparatus of claim 1, wherein the nozzle keeps a dilution factor in an optimal range for exhaust gas investigations.

17. A process for controlling a gas quantity setting system comprising the steps of:

drawing a dilution gas into a tubular flow element;

receiving an exhaust gas in said tubular flow element;

mixing said dilution gas and said exhaust gas thereby forming a mixture;

sensing a pressure and a temperature of the mixture;

sampling the mixture;

drawing the mixture toward a cross-sectionally variable venturi nozzle having an axially adjustable conical, nozzle needle; and adjusting a position of said conical nozzle needle with respect to said venturi nozzle taking into account the sensed pressure and temperature wherein a dilution ratio of the exhaust gas has a constant value despite fluctuations in a feeding quantity of the exhaust gas.

18. The method of claim 17 further comprising the steps of:

maintaining the dilution gas in a predetermined temperature range;

measuring a mass rate of flow of the dilution gas; and compensating for abrupt exhaust gas changes by controlling the position of the conical nozzle needle in response to fuzzy-control superpositioning dependent upon a characteristic of the nozzle and an optimal value of the dilution factor.

* * * * *